US00PP21393P2

(12) United States Plant Patent
McDonald

(10) Patent No.: US PP21,393 P2
(45) Date of Patent: Oct. 19, 2010

(54) ***ANISODONTEA* PLANT NAMED "NUANILAINP"**

(50) Latin Name: *Anisodontea hybrida*
Varietal Denomination: Nuanilainp

(75) Inventor: Daniel Bede McDonald, Seven Hills (AU)

(73) Assignee: Amerinova Properties LLC, Bonsall, CA (US)

( * ) Notice: Subject to any disclaimer, the term of this patent is extended or adjusted under 35 U.S.C. 154(b) by 0 days.

(21) Appl. No.: 12/387,036

(22) Filed: Apr. 27, 2009

(51) Int. Cl.
*A01H 5/00* (2006.01)

(52) U.S. Cl. ..... Plt./263.1

(58) Field of Classification Search ..... Plt./263.1, Plt./226

See application file for complete search history.

*Primary Examiner*—Annette H Para
(74) *Attorney, Agent, or Firm*—C. A. Whealy

(57) ABSTRACT

A new and distinct cultivar of *Anisodontea* plant named 'Nuanilainp', characterized by its compact, upright and outwardly spreading plant habit; freely branching habit; dense and bushy plant form; early and freely flowering habit; lavender pink and red purple bi-colored flowers; and good garden performance.

1 Drawing Sheet

Botanical designation: *Anisodontea hybrida.*
Cultivar denomination: 'Nuanilainp'.

BACKGROUND OF THE INVENTION

The present invention relates to a new and distinct cultivar of *Anisodontea* plant, botanically known as *Anisodontea hybrida*, and hereinafter referred to by the name 'Nuanilainp'.

The new *Anisodontea* plant is a product of a planned breeding program conducted by the Inventor in Cobbitty, New South Wales, Australia. The objective of the breeding program is to create new early and freely-flowering *Anisodontea* cultivars with compact plant habit, tolerance to high temperatures and attractive flower coloration.

The new *Anisodontea* plant originated from a cross-pollination made by the Inventor in Cobbitty, New South Wales, Australia in September, 2004, of a proprietary *Anisodontea hybrida* selection identified as code number X03.4.1, not patented, as the female, or seed, parent with a proprietary *Anisodontea hybrida* identified as code number X03.4.7, not patented, as the male, or pollen, parent. The new *Anisodontea* was discovered and selected by the Inventor as a single flowering plant from within the progeny of the stated cross-pollination in a controlled environment in Cobbitty, New South Wales, Australia in September, 2005.

Asexual reproduction of the new *Anisodontea* plant by terminal cuttings in a controlled environment in Cobbitty, New South Wales, Australia since October, 2005, has shown that the unique features of this new *Anisodontea* plant are stable and reproduced true to type in successive generations.

SUMMARY OF THE INVENTION

Plants of the new *Anisodontea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Nuanilainp'.

These characteristics in combination distinguish 'Nuanilainp' as a new and distinct cultivar of *Anisodontea:*

1. Compact, upright and outwardly spreading plant habit.
2. Freely branching habit; dense and bushy plant form.
3. Early and freely flowering habit.
4. Lavender pink and red purple bi-colored flowers.
5. Good garden performance.

Plants of the new *Anisodontea* can be compared to plants of the female parent selection. Plants of the new *Anisodontea* differ from plants of the female parent selection in the following characteristics:

1. Plants of the new *Anisodontea* are shorter than plants of the female parent selection.
2. Plants of the new *Anisodontea* have lighter-colored flowers than plants of the female parent selection.

Plants of the new *Anisodontea* can be compared to plants of the male parent selection. Plants of the new *Anisodontea* differ from plants of the male parent selection in the following characteristics:

1. Plants of the new *Anisodontea* are shorter than plants of the male parent selection.
2. Plants of the new *Anisodontea* have darker-colored flowers than plants of the male parent selection.

Plants of the new *Anisodontea* can be compared to plants of the *Anisodontea scabrosa*×*Anisodontea elegans* 'Elegant Lady', disclosed in U.S. Plant Pat. No. 16,301. In side-by-side comparisons conducted in Cobbitty, New South Wales, Australia, plants of the new *Anisodontea* differed from plants of 'Elegant Lady' in the following characteristics:

1. Plants of the new *Anisodontea* were shorter than plants of 'Elegant Lady'.
2. Flowers of plants of the new *Anisodontea* and 'Elegant Lady' differed in flower color as plants of 'Elegant Lady' had light purple-colored flowers.

Plants of the new *Anisodontea* can also be compared to plants of the *Anisodontea hybrida* 'Very Cranberry', not patented. In side-by-side comparisons conducted in Cobbitty, New South Wales, Australia, plants of the new *Anisodontea* differed from plants of 'Very Cranberry' in the following characteristics:

1. Plants of the new *Anisodontea* were shorter than plants of 'Very Cranberry'.

2. Flowers of plants of the new *Anisodontea* and 'Very Cranberry' differed in flower color as plants of 'Very Cranberry' had crimson-colored flowers.

BRIEF DESCRIPTION OF THE PHOTOGRAPHS

The accompanying colored photographs illustrate the overall appearance of the new *Anisodontea* plant, showing the colors as true as it is reasonably possible to obtain in colored reproductions of this type. Colors in the photographs may differ slightly from the color values cited in the detailed botanical description which accurately describe the colors of the new *Anisodontea* plant.

The photograph at the bottom of the sheet comprises a side perspective view of a typical flowering plant of 'Nuanilainp' grown in a container.

The photograph at the top of the sheet comprises a close-up view of typical flowers of 'Nuanilainp'.

DETAILED BOTANICAL DESCRIPTION

The aforementioned photographs and following observations, measurements and values describe plants grown in Bonsall, Calif. with three plants per container in a polyethylene-covered greenhouse during the winter and under conditions which closely approximate commercial production. During the production of the plants, day temperatures averaged 29° C. and night temperatures averaged 18° C. Plants were pinched one time and were ten weeks old when the photographs and the description were taken. In the following description, color references are made to The Royal Horticultural Society Colour Chart, Fifth Edition, except where general terms of ordinary dictionary significance are used.

Botanical classification: *Anisodontea hybrida* 'Nuanilainp'.

Parentage:

*Female, or seed, parent.*—Proprietary selection of *Anisodontea hybrida* identified as code number X03.4.1, not patented.

*Male or pollen parent.*—Proprietary selection of *Anisodontea hybrida* identified as code number X03.4.7, not patented.

Propagation:

*Type.*—By terminal cuttings.

*Time to initiate roots, summer.*—About ten days at temperatures of 24° C. to 26° C.

*Time to initiate roots, winter.*—About two weeks at temperatures of 24° C. to 26° C.

*Time to develop roots, summer.*—About three weeks at temperatures of 24° C. to 26° C.

*Time to develop roots, winter.*—About eight weeks at temperatures of 18° C. to 20° C.

*Root description.*—Medium in thickness, fibrous; white in color.

*Rooting habit.*—Moderately branching; moderately dense.

Plant description:

*Plant form and growth habit.*—Compact, upright and outwardly spreading plant habit; vigorous growth habit.

*Branching habit.*—Freely branching habit, usually about seven to eight primary lateral branches develop per plant each primary lateral with numerous secondary lateral branches; bushy and dense plant form.

*Plant height.*—About 42 cm.

*Plant diameter* (*area of spread*).—About 54 cm.

Lateral branch description:

*Length.*—About 36 cm.

*Diameter, at the base.*—About 6 mm.

*Internode length.*—About 3.2 cm.

*Texture.*—Pubescent.

*Strength.*—Strong.

*Color, immature.*—Close to 146B.

*Color, mature.*—Close to N199A.

Foliage description:

*Arrangement.*—Alternate, simple.

*Length.*—About 4.2 cm.

*Width.*—About 4.4 cm.

*Shape.*—Tri-lobed.

*Apex.*—Rounded and mucronate.

*Base.*—Obtuse to attenuate.

*Margin.*—Crenate; slightly serrate.

*Texture, upper and lower surfaces.*—Pubescent.

*Venation pattern.*—Palmate; reticulate.

*Color.*—Developing leaves, upper and lower surfaces: Close to 146B. Fully developed leaves, upper surface: Close to 137A; venation, close to 137A. Fully developed leaves, lower surface: Close to 147B; venation, close to 147C.

*Petiole.*—Length: About 1.5 cm. Diameter: About 1.5 mm. Texture, upper and lower surfaces: Pubescent. Color, upper and lower surfaces: Close to 137C.

Flower description:

*Flower arrangement.*—Single axillary flowers; freely flowering habit with usually about three or four open flowers and about 18 flower buds per lateral branch; flowers face upright or outwardly.

*Natural flowering season.*—Plants flower continuously throughout the summer in California; early flowering habit, plants begin flowering about ten weeks after planting.

*Flower longevity.*—Flowers last about five days on the plant; flowers persistent.

*Fragrance.*—None detected.

*Flower diameter.*—About 3.8 cm.

*Flower length* (*height*).—About 1.8 cm.

*Flower bud.*—Length: About 1.5 cm. Diameter: About 1 cm. Shape: Ovoid. Color: Close to 75D.

*Petals.*—Arrangement: Corolla consists of five petals in a single whorl. Length: About 1.7 cm. Width: About 1.6 cm. Shape: Obovate to obcordate. Apex: Rounded with a shallow notch. Base: Attenuate. Margin: Entire. Texture, upper and lower surfaces: Smooth, glabrous, satiny. Color: When opening, upper surface: Close to 84C. When opening, lower surface: Close to 84D. Fully opened, upper surface: Close to 84B; towards the base, close to 60B; venation, close to 60B; color becoming closer to 84C with development. Fully opened, lower surface: Close to 84B; color does not fade with development.

*Sepals.*—Appearance: Five sepals fused into a star-shaped calyx. Length: About 1.4 cm. Width: About 5 mm. Shape: Elliptical. Apex: Acuminate. Margin: Entire. Texture, upper and lower surfaces: Pubescent. Color, upper and lower surfaces: Close to 144A.

*Peduncles.*—Length: About 2.5 cm. Diameter: About 1 mm. Angle: About 30° to 45° from stem axis. Strength: Strong. Texture: Pubescent. Color: Close to 138A.

*Reproductive organs.*—Androecium: Stamen number: About 76. Filament length: About 2.5 mm. Filament color: Close to 85D. Anther shape: Rounded. Anther length: About 1 mm. Anther color: Close to N92B. Amount of pollen: Moderate. Pollen color: Close to 97C. Gynoecium: Pistil length: About 1.6 cm. Style length: About 8 mm. Style color: Close to 76D. Stigma appearance: Multi-parted. Stigma color: Close to 60A. Ovary color: Close to 145C.

*Seed/fruit.*—Seed and fruit production has not been observed.

Garden performance: Plants of the new *Anisodontea* have been observed to have good garden performance and to tolerate rain, wind and temperatures ranging from about 4° C. to about 43° C.

Pathogen/pest resistance: Plants of the new *Anisodontea* have not been shown to be resistant to pathogens and pests common to *Anisodontea.*

It is claimed:

1. A new and distinct *Anisodontea* plant named 'Nuanilainp' as illustrated and described.

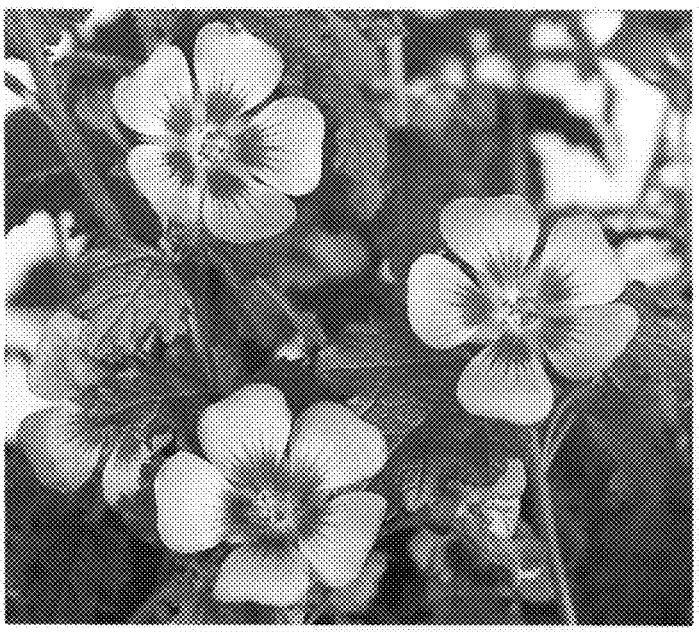
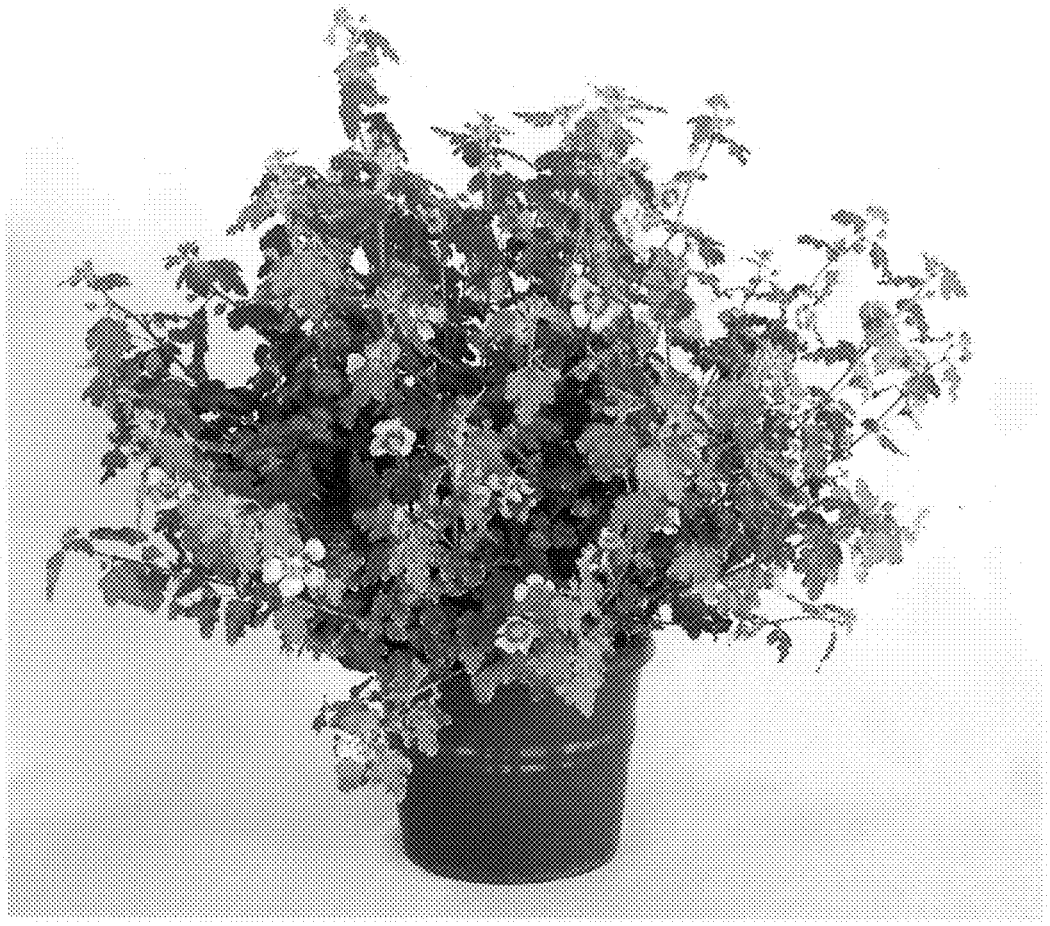

* * * * *